United States Patent
Karagianni et al.

(10) Patent No.: US 9,119,849 B2
(45) Date of Patent: *Sep. 1, 2015

(54) SUBSTITUTED GUAR PROTEIN EXTRACTS AND PRODUCTION/APPLICATIONS THEREOF

(75) Inventors: Katerina Karagianni, Paris (FR); Vincent Monin, Plainsboro, NJ (US); Jean-François Sassi, Saint-Romain en Jarez (FR)

(73) Assignee: RHODIA CHIMIE, Aubervilliers (FR)

( * ) Notice: Subject to any disclaimer, the term of this patent is extended or adjusted under 35 U.S.C. 154(b) by 1839 days.

This patent is subject to a terminal disclaimer.

(21) Appl. No.: 11/990,011

(22) PCT Filed: Aug. 7, 2006

(86) PCT No.: PCT/FR2006/001913
§ 371 (c)(1),
(2), (4) Date: Dec. 29, 2009

(87) PCT Pub. No.: WO2007/017590
PCT Pub. Date: Feb. 15, 2007

(65) Prior Publication Data
US 2010/0093933 A1 Apr. 15, 2010

(30) Foreign Application Priority Data
Aug. 5, 2005 (FR) ...................... 05 08380

(51) Int. Cl.
| | |
|---|---|
| A61K 36/00 | (2006.01) |
| A61K 31/736 | (2006.01) |
| A61K 36/48 | (2006.01) |
| A01N 25/10 | (2006.01) |
| A23L 1/30 | (2006.01) |
| A23L 1/305 | (2006.01) |
| A61K 8/64 | (2006.01) |
| A61Q 5/02 | (2006.01) |
| A61Q 5/12 | (2006.01) |
| A61Q 19/10 | (2006.01) |
| C10M 149/14 | (2006.01) |
| C02F 1/54 | (2006.01) |

(52) U.S. Cl.
CPC ............... *A61K 36/48* (2013.01); *A01N 25/10* (2013.01); *A23L 1/3002* (2013.01); *A23L 1/3055* (2013.01); *A61K 8/645* (2013.01); *A61Q 5/02* (2013.01); *A61Q 5/12* (2013.01); *A61Q 19/10* (2013.01); *C10M 149/14* (2013.01); *C02F 1/54* (2013.01); *C02F 2305/04* (2013.01); *C10M 2209/12* (2013.01); *C10M 2217/06* (2013.01); *C10N 2260/09* (2013.01)

(58) Field of Classification Search
None
See application file for complete search history.

(56) References Cited

U.S. PATENT DOCUMENTS

| | | | |
|---|---|---|---|
| 2001/0051140 A1* | 12/2001 | Wielinga et al. | ............. 424/70.1 |
| 2003/0147826 A1 | 8/2003 | Anthony et al. | |

FOREIGN PATENT DOCUMENTS

| | | |
|---|---|---|
| FR | 2437829 | 4/1980 |
| WO | WO 89/07435 A2 | 8/1989 |
| WO | WO 9835026 A1 * | 8/1998 |
| WO | WO 01/93810 A2 | 12/2001 |

OTHER PUBLICATIONS

Bertling, Hidden food allergens concerning the knowledge of guar, Allergologie, 1986, 9 (9): 413-415.*
Verma et al, Chemical, biochemical and microbiological examination of guar meal, Indian journal of poultry science, Sep. 1984. vol. 19, No. 3. p. 165-170.*
Khalil, Biochemical and technological studies on the production of isolated guar protein. Die Nahrung, (Feb. 2001) vol. 45, No. 1, pp. 21-24.*
Trimble "The Possible Utilization of Guar Protein", Proceedings International Congress Food Science and Technology, 1983, pp. 29-30, vol. 1.
Nath et al., "Functional Properties of Guar Proteins", Journal of Food Science, 1981, pp. 1255-, vol. 46, No. 4, Chicago, IL.
Khalil, "Biochemical and technological studies on the production of isolated guar protein", Nahrung/Food, 2001, pp. 21-24, vol. 45, No. 1, Wiley-VCH Verlag GmbH, Weinhelm.

* cited by examiner

*Primary Examiner* — Qiuwen Mi
(74) *Attorney, Agent, or Firm* — Dentons US LLP

(57) ABSTRACT

A variety of products are obtained from modified guar protein extracts, for example, cosmetic or pharmacological or plant protective compositions or domestic care agents containing such products; these are particularly suitable for treating and/or modifying and/or coating the skin, hair, hard and textile surfaces and, notably, plant leaf surfaces.

18 Claims, No Drawings

SUBSTITUTED GUAR PROTEIN EXTRACTS AND PRODUCTION/APPLICATIONS THEREOF

CROSS-REFERENCE TO PRIORITY/PCT APPLICATIONS

This application claims priority under 35 U.S.C. §119 of FR 0508380, filed Aug. 5, 2005, and is a continuation of PCT/FR 2006/001913, filed Aug. 7, 2006 and designating the United States (published in the French language on Feb. 15, 2007, as WO 2007/017590 A2; the title and abstract were published in English), each hereby expressly incorporated by reference in its entirety and each assigned to the assignee hereof.

The present invention relates to products obtained from a modified guar protein extract, the process for the preparation thereof, and the cosmetic, pharmacological, phytosanitary or household treatment compositions comprising them. These products and the formulations thereof are of particular benefit in the field of cosmetics, specifically for producing hairstyling products, for the shaping of hair, or for producing shampoos, conditioners or shower gels, for conditioning the skin and/or hair. They are also of interest in the field of detergency, specifically for household treatments.

The use of guar extracts is known; for example, the use of guar gum or of guar derivatives in the fields of cosmetics and foods, specifically as an agent for modifying the rheology and/or texture of a composition or a food, or as a skin and/or hair conditioner.

The protein fractions contained in the guar gum or in flours extracted from guar have also been described (Anderson et al., *Food Additives and Contaminants*, 1985, vol. 2, No. 4, 225-230; Nath et al., *J. Agric. Food Chem.*, 1980, 28, 844-847). M. M. Khalil (Production of Isolated Guar Protein, *Food* 45, 2001, No. 1, 21-24) took a particular interest in the nutritional qualities of proteins isolated from guar seed flour.

Furthermore, there is a constant need in industry for new compositions, for example comprising new products able to display new properties or to improve properties. In particular, there is a great interest in products originating from plants.

It has now been found that when chemical groups are grafted onto the proteins contained in the guar protein extract, a product having beneficial properties for skin and skin appendages, specifically hair, is obtained. Such derivative guar protein extracts are thus particularly useful in cosmetic care and in pharmacology, in particular in dermatology. More specifically, it has been found that this grafted product has excellent hair and skin conditioning properties. Moreover, the extract is easily formulated. This can make its use simple and inexpensive.

Thus, it has been found that the cationised guar protein extract is compatible with the majority of anionic surfactants routinely used in the field of cosmetic, pharmacological, phytosanitary and detergency products, for a wide range of compositions.

It has likewise been found that these products may be used in compositions for household treatments (for treatments carried out by consumers in the private sphere, as well as for treatments carried out in the public sphere, such as the industrial or institutional cleaning of surfaces and textiles), in particular detergent compositions, specifically for the treatment, for example cleaning, of hard surfaces, including crockery, or of textile surfaces. More specifically, these compositions soften and facilitate the ironing of fabrics. They also allow the cleaning of hard surfaces to be facilitated.

Surprisingly, it has also been found that it is possible to decrease the rebound of drops and to increase the retention of phytosanitary formulations and/or nutritional elements by introducing derivative guar protein extracts into said formulations applied to plants. The derivative guar protein extracts have a positive effect on the instantaneous adhesion and, as a result, on the retention of spray drops, in conditions with large particle sizes. Advantageously, these extracts significantly reduce the phenomenon of rebound, usually observed in the case of a spray in the form of drops of large particle size, and in addition, limit the phenomenon of runoff. The derivative guar protein extracts thus improve the instantaneous adhesion and, as a result, the phytosanitary retention and/or the retention of nutritional elements when applied in the form of droplets to the plants to be treated.

DEFINITIONS

In the present application, guar designates the plant *Cyanopsis tetragonoloba*. In the present document, the percentages by weight are expressed in terms of dry weight, unless stated otherwise.

In the present application, "guar seeds" designates seeds obtained from guar. Guar seeds comprise the hull, which is more or less fibrous, the germ, and two "guar splits" or "endosperm halves", which constitute the endosperm of guar. The splits (or endosperm) is/are rich in galactomannes. The guar seeds generally consist of 35 to 40% by weight of endosperm, 42 to 47% by weight of germ, and 14 to 17% by weight of hull.

In the present application, "guar flour" or "guar powder" designates a powder obtained from the guar endosperm.

In the present application, "native guar" designates macromolecular chains of the galactomannan type, obtained from guar endosperm, not having been subjected to chemical modification by the grafting of chemical groups. Native guar comprises macromolecules containing a principal chain of D-mannopyranose units linked in the beta (1-4) position substituted by D-galactopyranose units in the beta (1-6) position. Native guar has a mannose/galactose ratio of about 2. The native guar may optionally have been partially depolymerised (a reduction in the molecular mass). By "derivatized guar" are meant macromolecular chains obtained from native guar, having undergone a chemical modification via the grafting of chemical groups.

In the present application, "guar gum" designates a product substantially consisting of native guar, in the form of guar splits, or of guar flour or powder.

Guar germ generally comprises 35 to 45% by weight of proteins, 30 to 35% by weight of fibers, less than 5% galactomannans, about 5% salts, about 5-10% water, about 6% fats, the percentages by weight being expressed based on the total weight of the guar germ. Guar germ ("churi" in the language used notably in the cultural basins of India and Pakistan) is sometimes improperly designated by the term "guar protein". In the present application, "guar protein" does not designate guar germ.

The guar splits comprise about 4 to 6% protein.

The guar hull generally does not comprise any proteins (about 0% by weight). The guar hull is sometimes designated as "korma" in the language used notably in the cultural basins of India and Pakistan The guar gum is obtained by a process including finer or less fine separation of a product comprising guar splits, on the one hand, (possibly with some impurities) and of a by-product comprising the hull and the germ, on the other hand (possibly with some impurities). The process is generally substantially mechanical, but washing and/or extraction steps, aided by water or solvents or bulking agents, as well as purification steps with acidic or alkaline agents, may come in between. These processes, steps, products and by-products are known to the person skilled in the art.

In the present application, "guar meal" designates the by-product obtained from the recovery of the splits, typically comprising about 70-80° A) by weight of guar germ ("churn") and about 20-30° A) by weight of hull ("korma") and less than 10% by weight of endosperm.

In the present application, "guar protein extract" or "guar protein" designates a product comprising at least 65% by weight of proteins, typically 65 to 95% by weight, extracted from guar germ, typically obtained by a process of concentration and/or extraction and/or isolation starting from guar meal. In the present application, a "guar protein isolate" or a "guar protein concentrate" may also be referred to.

In the present application, unless stated otherwise, the quantities of proteins by weight are determined from the nitrogen level, measured according to the known Kjeldahl method. The nitrogen level is multiplied by 6.25 to obtain the quantity of protein by weight.

In the present application, "derivatized guar protein extract" or "derivatized guar protein" designates a product which can be obtained by chemical modification of the molecules of the guar protein extract. In other words, it is a product comprising guar proteins modified by chemically grafted groups.

According to a first aspect, the invention therefore relates to a product obtained from a guar protein extract, characterised in that it comprises chemical groups covalently grafted onto amino acid functional groups contained in the protein extract, said protein extract being obtained specifically from guar meal.

The amino acid composition and the biodistribution of the molecular mass of the protein extract can vary, to a greater or lesser extent, depending on the origin of the guar seeds, their maturation, and the conditions used for extraction.

The amino acids present in the guar protein extract include, principally, glutamic acid (Glu), arginine (Arg), aspartic acid (Asp), leucine (Leu), glycine (Gly), serine (Ser) and proline (Pro).

The guar protein extract may thus comprise:
10% to 30% glutamic acid, specifically 15% to 25%;
5% to 25% arginine, specifically 10% to 20%, and more particularly 12% to 16%;
5% to 20° A) aspartic acid, specifically 10% to 15%;
1% to 10% leucine, and specifically 5% to 10%;
1% to 8% glycine, and specifically 4° A) to 6%;
the percentages being expressed by mass based on the total mass of amino acids contained in the extract.

Preferably, the guar protein extract comprises the following amino acid compositions:

| Amino acids | % |
|---|---|
| cysteine | 1.38 |
| methionine | 1.19 |
| aspartic acid | 10.90 |
| threonine | 2.75 |
| serine | 4.83 |
| glutamic acid | 22.97 |
| proline | 4.21 |
| glycine | 5.19 |
| alanine | 3.32 |
| valine | 3.51 |
| isoleucine | 3.18 |

-continued

| Amino acids | % |
|---|---|
| leucine | 6.21 |
| tyrosine | 3.70 |
| phenylalanine | 4.14 |
| lysine | 3.78 |
| histidine | 2.89 |
| arginine | 14.41 |
| tryptophan | 1.44 | the percentages being expressed by mass based on the total mass of amino acids contained in the isolated protein sample.

The guar protein extract thus has a relatively large quantity of arginine, compared with the proteins routinely used in the field of cosmetics, such as soya proteins, milk proteins or oat proteins. Now, arginine is an amino acid which is particularly useful in the field of cosmetics, since it has, for example, a moisturising action on skin.

Without a limitation to any one theory, chemical groups can be grafted specifically onto the —OH or —NH$_2$ or —COOH functional groups carried on the side chains of amino acids and/or the terminal functional groups of proteins.

Preferably, the protein extract contains 65 to 95% proteins, and specifically 65 to 85% by weight of proteins.

The guar protein extract in the form of a derivative can, typically, have the same division into amino acids as the non-derivatized extract, optionally with lower molar masses.

Chemical groups which can be grafted onto the amino acids in the protein extract include:

cationic or cationisable groups. By "cationisable groups" are meant groups which are potentially cationic, i.e. which can become cationic depending on the pH of the medium.

anionic or anionisable groups. By "anionisable groups" are meant groups which are potentially anionic, i.e. which can become anionic depending on the pH of the medium.

uncharged hydrophilic or hydrophobic groups. The guar protein extract derivatized by uncharged hydrophobic groups may have a surfactant characteristic.

groups cross-linking the guar protein extract, optionally polymeric groups. In the last case, "cross-polymers" derived from the guar protein extract may be referred to.

Note that the hydrogen atom is not a chemical group within the meaning of the present description.

It is possible to combine a plurality of modifications, for example hydrolysis and grafting. It is possible to combine the grafting of several different groups.

Cationic or Potentially Cationic Derivatives

The cationic or cationisable groups include the groups comprising quaternary ammoniums or tertiary amines, pyridiniums, guanidiniums, phosphoniums or sulphoniums.

The cationic products according to the invention can be obtained by causing the proteins of the guar protein extract to react in the conventional manner, as they are or after they have been subjected to enzymatic or chemical hydrolysis so as to cleave the peptide bonds.

Cationisation by Nucleophilic Substitution

The introduction of cationic or cationisable groups into the guar protein extract can be carried out by a nucleophilic substitution reaction.

If it is desired to introduce an ammonium group, the suitable reagent used may be:

3-chloro-2-hydroxypropyl trimethylammonium chloride, sold under the name of QUAB 188 by the company DEGUSSA;

an epoxide carrying a quaternary ammonium, such as 2,3-epoxypropyl trimethylammonium chloride, sold under the name of QUAB 151 by the company DEGUSSA, or similar compositions;

diethylaminoethyl chloride;

or Michael acceptor groups such as, for example, acrylates or methacrylates carrying quaternary ammoniums or tertiary amines.

Cationisation by Esterification

The introduction of cationic or cationisable groups into the amino acids of the guar protein extract may be carried out via esterification with amino acids such as, for example, glycine, lysine, arginine, 6-aminocaproic acid, or with derivatives of quaternised amino acids such as, for example, betaine hydrochloride.

Cationisation by Radical Polymerisation

The introduction of cationic or cationisable groups into the guar protein extract may be carried out via a radical polymerisation, involving the grafting of monomers comprising at least one cationic or cationisable group onto the amino acids of the guar protein extract.

The radical initiation may be carried out using cerium as described in the publication *European Polymer Journal, vol. 12*, p. 535-541, 1976. The radical initiation may also be carried out with ionising radiation and in particular by bombardment with an electron beam.

The monomers comprising at least one cationic or cationisable group used to carry out this radical polymerisation may be, for example, monomers comprising at least one ethylenic unsaturation and at least one atom of nitrogen which is quaternary or quaternisable by adjusting the pH.

These monomers comprising at least one ethylenic unsaturation and at least one atom of nitrogen which is quaternary or quaternisable by adjusting the pH include the following compounds of formulae (I), (II), (III), (IV) or (V):

the compound of general formula (I)

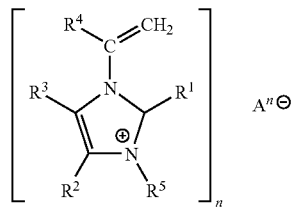

(I)

wherein:

$A^{n\ominus}$ represents a $Cl^{\ominus}$, $Br^{\ominus}$, $I^{\ominus}$, $SO_4^{2\ominus}$, $CO_3^{2\ominus}$, $CH_3$—$OSO_{3\ominus}$, $OH^{\ominus}$ or $CH_3$—$CH_2$—$OSO_3^{\ominus}$ ion, $R^1$ to $R^5$ are the same or different and represent, independently of one another, an alkyl group containing 1 to 20 carbon atoms, a benzyl radical or an H atom, and n=1 or 2, or the compound of general formula (II)

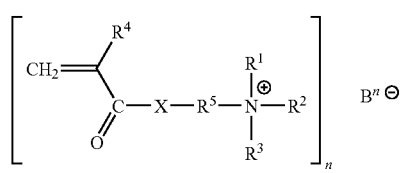

(II)

wherein:

X represents a —NH group or an oxygen atom O, $R^4$ represents a hydrogen atom or an alkyl group containing 1 to 20 carbon atoms, $R^5$ represents an alkene group containing 1 to 20 carbon atoms, $R^1$, $R^2$, $R^3$ are the same or different and represent, independently of one another, an alkyl group containing 1 to 20 carbon atoms, $B^{n\ominus}$ represents a $Cl^{\ominus}$, $Br^{\ominus}$, $I^{\ominus}$, $SO_4^{2\ominus}$, $CO_3^{2\ominus}$, $CH_3$—$OSO_{3\ominus}$, $OH^{\ominus}$ or $CH_3$—$CH_2$—$OSO_3^{\ominus}$ ion, and n=1 or 2, or the compound of general formula (III)

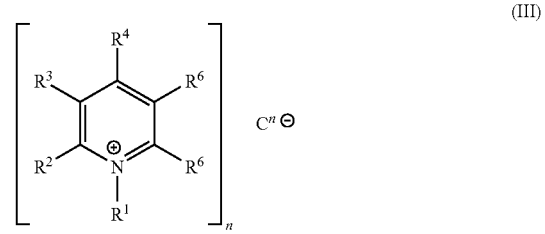

(III)

wherein:

$R^1$ to $R^6$ are the same or different and represent, independently of one another, a hydrogen atom or an alkyl group containing 1 to 20 carbon atoms, but with one of the groups $R^1$ to $R^6$ representing a —CH=$CH_2$ group, $C^{n\ominus}$ represents a $Cl^{\ominus}$, $Br^{\ominus}$, $I^{\ominus}$, $SO_4^{2\ominus}$, $CO_3^{2\ominus}$, $CH_3$—$OSO_{3\ominus}$, $OH^{\ominus}$ or $CH_3$—$CH_2$—$OSO_{3\ominus}$ ion, and n=1 or 2, or the compound of general formula (IV)

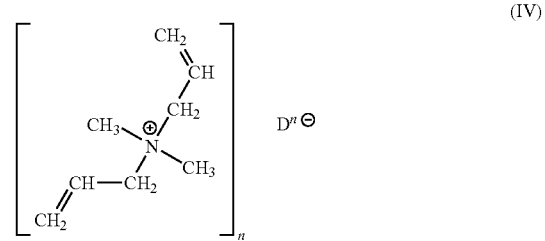

(IV)

wherein:

$D^{n\ominus}$ represents a $Cl^{\ominus}$, $Br^{\ominus}$, $I^{\ominus}$, $SO_4^{2\ominus}$, $CO_3^{2\ominus}$, $CH_3$—$OSO_{3\ominus}$, $OH^{\ominus}$ or $CH_3$—$CH_2$—$OSO_{3\ominus}$ ion, and n=1 or 2.

Preferably, the monomers comprising at least one ethylenic unsaturation and at least one quaternary or quaternisable nitrogen atom are selected from:

2-dimethylaminoethyl acrylate (DMAA), quaternised 2-dimethylaminoethyl acrylate (Quat-DMAA), 2-dimethylaminoethyl methacrylate (DMAMA), quaternised 2-dimethylaminoethyl methacrylate (Quat-DMAMA), quaternised 2-diethylaminoethyl methacrylate chloride, called Pleximon 735 or TMAE MC 80 by the company Röhm, diallyldimethylammonium chloride (DADMAC)

methacrylamidopropyl trimethylammonium chloride, called MAPTAC, or mixtures thereof.

The cationic derivatized guar protein extract may contain cationic or cationisable units, obtained from a chemical transformation, after polymerisation, of precursor monomers of cationic or cationisable functional groups. Poly-p-chloromethylstyrene, which forms quaternised polyparatrimethyl aminomethyl styrene after reaction with a tertiary amine such as a trimethyl amine, can be mentioned here by way of example.

The cationic or cationisable units are combined with negatively charged counter ions. These counter ions may be selected from chloride, bromide, iodide, fluoride, sulphate, methylsulphate, phosphate, hydrogenophosphate, phosphonate, carbonate, hydrogenocarbonate, or hydroxide ions.

Preferably, counter ions selected from hydrogenophosphates, methylsulphates, hydroxides and chlorides are used.

The degree of substitution of the cationic modified guar protein extracts according to the invention is at least 0.01 and preferably at least 0.05.

If the degree of substitution is less than 0.01, the effectiveness of the fixing of the protein extract on the surface to be treated can be reduced.

If the degree of substitution is greater than 0.05, the effectiveness in terms of affinity for the surface can be distinctly improved.

The degree of substitution of the modified cationic guar protein extract corresponds to the mean number of cationic charges introduced by amino acid. Said degree of substitution may be determined by elemental analysis, for example of the nitrogen.

Anionic or Potentially Anionic Derivatives

The anionic or potentially anionic (anionisable) groups can be obtained by reaction with an anionising agent such as propane saltone, butane saltone, monochloroacetic acid, chlorosulphonic acid, maleic acid anhydride, succinic acid anhydride, citric acid, sulphates, sulphonates, phosphates, phosphonates, orthophosphates, polyphosphates, metaphosphates and similar.

Uncharged Hydrophilic or Hydrophobic Derivatives

The hydrophilic groups include in particular one or more saccharide or oligosaccharide residues, one or more ethoxy groups, one or more hydroxyethyl groups, or one or more oligoethylene oxides.

The hydrophobic groups which may be introduced include in particular an alkyl, aryl, phenyl, benzyl, acetyl, hydroxybutyl or hydroxypropyl group, or a mixture thereof. Fatty acid groups may also be mentioned, a fatty acid being grafted onto amino acid functional groups. By alkyl or aryl or acetyl radical are meant alkyl or aryl or acetyl radicals containing 1 to 22 carbon atoms.

Cross-Linked Derivatives

Cross-linking groups may be introduced by chemical cross-linking. The chemical cross-linking of starch may be achieved by the action of a cross-linking agent selected from formaldehyde, glyoxal, halohydrins such as epichlorohydrin or epibromohydrin, phosphorus oxychloride, polyphosphates, diisocyanates, diethylene urea, polyacids such as adipic acid, citric acid, acrolein and similar. Chemical cross-linking may also be achieved by the action of a metallic complexing agent such as, for example, zirconium (IV). Chemical cross-linking may also be achieved under the effect of ionising radiation.

According to another aspect, the invention relates to a method for preparing a product obtained from guar protein extract, comprising the following steps:

a) preparation of a guar protein extract;
b) grafting reactions onto amino acid functional groups contained in the protein extract; and optionally
c) recovery of the product obtained.

The guar protein extract used in step a) may be prepared starting from guar seeds, or preferably starting from guar meal, according to the usual methods for extracting proteins from plants, particularly soya proteins. Methods of this type are described in the Kirk Othmer encyclopaedia, "Encyclopedia of Industrial Chemistry", vol. A22, pages 295 to 300 and pages 612 to 614.

The guar protein extract may specifically be isolated or concentrated starting from the guar meal, which is the by-product of the recovery of the splits of the guar seeds. Said guar meal is commercially available. It is, for example, sold by Rhodia under the name "Guar Meal" 100% or 31%. The guar meals may also be prepared according to the method disclosed by North J. P., Subramanian N., Narasinja Rao, M. S., *J. Agric. Food Chem.* 26 (5), 1243 (1978).

The guar protein extract may be prepared by the method known as "concentration". This method generally involves:

a1) suspending guar germs, preferably from a guar meal, in an extraction liquid;
b1) separating the solid phase S1 and recovering the liquid phase L1;
c1) adjusting the pH of the recovered liquid phase L1 to an acidic pH;
d1) recovering the protein extract in the form of a precipitate.

The guar germs used in step a1) of the process encompass the guar germs which might be present, for example in the guar seeds optionally without their hulls and/or ground into a powdered form, in the guar flours or in the guar meals. Preferably, in step a1), the guar meal is extracted.

The extraction liquid in step a1) may be selected from organic solvents, water, or a mixture thereof.

The organic solvents useful as an extraction liquid include alcohols such as ethanol, hydrocarbon solvents such as n-hexane, ethers such as diethyl ether.

The extraction liquid can also be water, preferably demineralised, and more preferably a solution at an alkaline pH, optionally in combination with an organic co-solvent, such as an alcohol.

The solutions at an alkaline pH are solutions of pH $>7$, specifically $>8$, and more particularly $>9$. They may in particular be solutions of alkali metal hydroxide, such as solutions of sodium hydroxide or potassium hydroxide.

The extraction medium may further contain mineral salts such as sodium chloride or potassium chloride.

The concentration of mineral salts in the extraction medium may vary to a great degree and is generally within the range of 0.5 M to 1.5 M.

The extraction may take place at a wide range of temperatures, specifically between 20° C. and 80° C., preferably between 40° C. and 60° C., and more preferably at about 55° C.

The extraction may be carried out with a ratio of guar meal:extraction liquid from 1:100 to 50:100 in terms of weight, preferably with a ratio from 2:100 to 25:100 in terms of weight.

The time required for the extraction may also vary considerably according to a number of factors, specifically the temperature of extraction and the liquid of extraction. A length of time generally between 10 minutes and 3 hours generally proves to be sufficient.

The crude extract obtained in step a1) is subsequently separated, for example by filtration or centrifuging. The solid phase S1, which is less protein-rich and may, for example, contain endosperm and/or hull, is removed, and the liquid phase L1, corresponding to the protein-rich extract, is recovered.

According to one variant, the solid S1 is recovered in turn and extracted with an extraction liquid which may be the same as or different from the extraction liquid used for the guar germs. The crude extract obtained is subsequently separated, and the liquid phase L2 is recovered.

The liquid phase(s) extracted, L1 or (L1+L2), is/are subsequently acidified by the addition of a concentrated solution of an inorganic acid such as hydrochloric acid. A sufficient quantity of this acid is added for the pH of the liquid L1 or L1+L2 to be adjusted to a value ≤7, in particular ≤5, and more specifically ≤4.

The precipitate which subsequently forms is recovered, for example by centrifuging or filtration.

It may then be dried, for example by concentration under vacuum, atomisation or lyophilisation. It should be noted that a particular fraction of the precipitate obtained may be purified or concentrated by liquid/liquid extraction by means of organic solvents or preparative chromatography.

According to a beneficial variant, the guar protein extract is prepared starting from guar meals or guar flours according to the technique termed "isolation technique". This method involves the steps used in the concentration step, except that the guar germs used in step a1), in the form of guar flours or guar meals, are previously protein-enriched by the steps of:

a2) sieving the guar flours or guar meals and recovering the particles of diameter less than 1,500 µm, specifically less than 1,400 µm;

b2) separating and recovering the heaviest particles contained in the guar flour or guar meal which has been sieved.

During step a2), a large proportion of the guar endosperm, low in protein, is removed.

Step b2) may be carried out according to conventional techniques, for example by means of a fluidised-bed dryer, equipped with a device for collecting the lightest particles carried by an air flow. This step thus allows the removal of the light particles, rich in fibre, and the recovery of the densest particles which are generally richer in proteins.

The grafting reactions onto the functional groups carried by amino acids contained in the guar protein extract can be carried out by the application or adaptation of the nucleophilic substitution, esterification, or radical polymerisation processes used thus far or described in the literature, for example those disclosed in R. C. Larock, *Comprehensive Organic Transformations*, VCH Publishers, 1989.

The protein extract obtained may be used as it is pursuant to the extraction process, which may lead to a partial depolymerisation of the proteins.

In a variant, before the grafting step b), the process may moreover involve chemical or enzymatic hydrolysis of the peptide bonds.

According to a preferred embodiment, the proteins have molecular masses lower than 30,000 Da, specifically of 100 to 30,000, preferably between 500 and 20,000, and more preferably of the order of 750 to 15,000 Da, which masses are particularly preferred in the field of cosmetic products. The hydrolysed proteins are in fact generally more substantive and penetrate more easily into the cortex of the hair or into the epidermis.

The enzymes useful in this protein depolymerisation step include, for example, proteases from animals, plants, microbes or fungi.

Examples of chemical reagents useful in this depolymerisation step include mineral bases, such as alkali metal or alkaline earth metal hydroxides, and inorganic acids such as hydrochloric acid.

Compositions—Uses

The composition for the modification and/or treatment of surfaces comprises modified guar protein extract, and generally other ingredients (or "constituents"). In particular, it generally comprises a carrier, most often a liquid, for topical application of cosmetic or pharmacological compositions.

Thus, useful compositions may be compositions for the treatment and/or modification of surfaces, comprising:

a liquid carrier, for example an aqueous, alcoholic or hydroxyalcoholic carrier, and the modified guar protein extract, optionally, at least one surfactant, for example an anionic, non-ionic, or amphoteric surfactant, or a mixture, optionally, other ingredients.

The composition may be used in a treatment or modification process on a surface, which involves the following steps:

applying the composition to the surface, and optionally, removing the carrier or diluting the composition or modifying the pH.

The target surfaces may specifically be:

the skin and/or hair, in the case of cosmetic compositions the teeth, in the case of compositions for buccal dental care, hard surfaces, including crockery, in the case of compositions for household treatments, for example the surfaces (metal, ceramics, plastics material, glass, etc.) of crockery, in the case of formulations intended for washing crockery by hand or in a dishwasher, floors (wood, ceramics, plastics material, concrete, etc.), in the case of compositions for multi-purpose cleaning or for cleaning floors, the surfaces found in kitchens, in the case of compositions for multi-purpose cleaning or for kitchen cleaning, the surfaces found in bathrooms, in the case of compositions for multi-purpose cleaning or for bathroom cleaning, window panes or windscreens, in the case of compositions for cleaning window panes or windscreens the skin, in the case of pharmacological compositions, the leaves of plants, in the case of phytosanitary compositions.

textile surfaces, in the case of compositions for cleaning and/or rinsing (for example in softening agents) and/or ironing clothing.

The application of a cosmetic composition according to the invention is preferably carried out topically.

The composition is intended more particularly for the treatment of skin or hair, and may be in the form of an ointment, cream, oil, milk, pomade, powder, soaked pad, solution, fluid; gel, spray, lotion, suspension, moulded product (soap, for example) or foam. Cosmetic compositions according to the invention may also be in the form of a simple oil-in-water or water-in-oil emulsion, a multiple emulsion, a micro-emulsion, an aqueous or hydroalcoholic gel.

Specifically, a shampoo, conditioner (rinse or non-rinse), a styling product (for shaping hair, for example) or a shower gel may be involved.

The cosmetic compositions may be compositions for the care and hygiene of skin and/or hair.

Examples of cosmetic compositions for the hair are, specifically, compositions for shampoo, conditioner, hair-styling products, or protection, repair, or softening products, or other compositions for permanent waving and colouring.

Without a limitation to any one theory, it has been found that modified guar protein extracts have a very strong affinity for hair, which could explain their substantial fixing properties, and specifically their resistance to humidity on dry hair.

Some examples of cosmetic compositions for the skin are, specifically, products for the face and body, day and night products, anti-sun products, anti-ageing or anti-wrinkle hygiene products, anti-pollution products, shower gels, and hand creams.

The cosmetic compositions according to the invention may comprise from 0.0001 to 4% of said extract in terms of the weight of the composition, preferably from 0.01 to 1%.

The guar proteins contained in the cosmetic compositions according to the invention may thus represent from 0.00003% to 4% by weight, specifically from 0.001% to 1% by weight, of the cosmetic composition.

Examples of detergent compositions are, specifically, compositions for domestic use and/or for household treatments, such as products for the treatment of textiles, such as detergents, softening agents, products for the upkeep of clothing, or other products for the treatment of hard surfaces, such as products for the cleaning or upkeep of floors.

The modified guar protein extracts according to the invention are particularly useful for the treatment of skin appendages, such as hair, or of skin, or of textiles or household surfaces, or even of plants, in particular of the leaf surface of plants.

The modified guar protein extracts may be used in combination with a cosmetically acceptable vehicle in compositions intended to clean and/or repair and/or protect skin, hair, or scalp.

The modified guar protein extracts may thus be used in combination with a cosmetically acceptable vehicle, to increase or improve the hydration, elasticity, or silkiness of skin, or even to firm up the skin.

They may also be used in combination with a cosmetically acceptable vehicle in anti-dandruff, hair restoration, and anti-hair-loss compositions, and in rehydrating, nourishing, and revitalising hair-care compositions. They may also be used in compositions intended for the protection of hair against damage due to cold, the sun, or pollution (called "winter care", "summer care", and "anti-pollution" compositions). Finally, they may be used in compositions intended to give volume, shine, lustre in the natural colour, or colouration, a pleasant feel, bounciness in the curls, or a sleek effect.

By "cosmetically acceptable vehicle" is meant a vehicle suitable for use in contact with human and animal cells, in particular the cells of the epidermis, without toxicity, irritation, induced allergic response or similar, and with a proportionally advantageous effect/reasonable risk.

The modified guar protein extracts can be used in detergents, softeners, household maintenance products, for example cleaning products for floors or household surfaces, and anti-dust products.

Advantageously, the products according to the invention have a softening and anti-crumpling effect where the treatment of textiles is concerned, or even an anti-marking, anti-stain effect where household surfaces are concerned.

Without a limitation to any one theory, the application of the products according to the invention would lead to hydrophilisation of the textile or household surfaces, which would allow the formation of markings during drying to be avoided, and the following cleaning to be made easier.

The modified guar protein extracts may be used in a phytosanitary composition and/or composition of nutritional elements designed to be sprayed onto the leaf surface of plants as an anti-rebound agent. This anti-rebound agent advantageously allows the instantaneous adhesion, and as a result the retention, and thus the effectiveness, of the sprayed composition to be improved:

Examples of phytosanitary compositions are formulations containing an active substance such as a herbicide, haulm killer, brush killer, bactericide, fungicide, insecticide, acaricide, or growth regulator.

Thus, the modified guar protein extracts allow the loss, onto the ground, of sprayed compositions to be limited, which loss can cause pollution of the soil and of underground water tables.

More fully, the products according to the invention or the modified guar protein extracts according to the invention can be used in:
  cosmetic compositions,
  pharmacological compositions,
  compositions for household treatments,
  coating compositions such as paints,
  food compositions for feeding humans,
  lubricant compositions,
  fluids used in oil and gas extraction,
  phytosanitary compositions,
  water treatment.

The products according to the invention or the modified guar protein extracts according to the invention can be used as:
  an agent for the treatment and/or modification of surfaces,
  a dispersing agent,
  an emulsifier,
  an agent to prevent rebound, washing away, or blowing away of phytosanitary
  formulations,
  an adhesive,
  a flocculant,
  a surfactant,
  an agent for altering the properties of foams,
  a foam stabiliser,
  an agent for modifying the appearance of a coating, and/or
  a thickener.

In the compositions, the guar protein extract, optionally in the form of a derivative, may have a foam-stabilising effect, in particular in foaming cosmetic compositions, or in compositions for the cleaning by hand of crockery or clothing.

Further details or benefits will emerge from the following examples, which are of a non-limiting nature.

EXAMPLE 1

Preparation of a "Guar Protein" Guar Protein Extract

A suspension containing 10% guar meal is prepared by dispersing 45.3 kg of guar meal (Rhodia, Vernon factory) in 454 l of water preheated to 55° C. The initial pH of the suspension is 4.85. 1,980 ml of 30% sodium hydroxide are added to raise the pH to 9.53. The suspension is stirred for 45 minutes at 55° C.

The suspension is centrifuged and 394.4 kg of liquid (1) and 107.7 kg of solid (2) are recovered. The solid (2) is not used again.

The pH of the liquid (1) is 8.62. 3,920 ml of 30% hydrochloric acid are added to lower the pH to 4.54, which leads to precipitation of the proteins. This suspension is stirred for 30 minutes at 45° C.

The suspension is centrifuged. The solid (3) is recovered and 310.5 kg of liquid (4) are removed.

The solid (3) is suspended again in water to be washed. A quantity of water approximately equal to the mass of the solid (3) is added. The pH of this suspension is 4.75.

This suspension is centrifuged. 46.3 kg of solid (4) and 110.7 kg of liquid (5) are recovered. The liquid (5) is not used again.

510 ml of 30% sodium hydroxide are added to the wet solid (4) to bring the pH to 6.94.

This solid is subsequently pasteurised by a thermal treatment at 90° C. for 20 seconds, then atomised. 6.8 kg of isolated guar proteins are thus obtained.

The sample of isolated protein contains:
71-72% proteins
5.6% ash (calcination)
6.6% fats (hydrolysis/extraction)
8.8% concentration in water [Karl Fischer]
Sugars (HPLC/Refractometry)
Fructose <0.1%
Glucose <0.1%
Sucrose 0.3%
Maltose <0.5%
Lactose <0.5%
Amino Acid Profile
Amino acid % by mass based on the total amino acid content of the isolated protein sample.

| Amino acids | % |
|---|---|
| cysteine | 1.38 |
| methionine | 1.19 |
| aspartic acid | 10.90 |
| threonine | 2.75 |
| serine | 4.83 |
| glutamic acid | 22.97 |
| proline | 4.21 |
| glycine | 5.19 |
| alanine | 3.32 |
| valine | 3.51 |
| isoleucine | 3.18 |
| leucine | 6.21 |
| tyrosine | 3.70 |
| phenylalanine | 4.14 |
| lysine | 3.78 |
| histidine | 2.89 |
| arginine | 14.41 |
| tryptophan | 1.44 |

Amino acid % by mass based on the whole sample of isolated protein.

| | |
|---|---|
| cysteine | 0.98 |
| methionine | 0.84 |
| aspartic acid | 7.72 |
| threonine | 1.95 |
| serine | 3.42 |
| glutamic acid | 16.27 |
| proline | 2.98 |
| glycine | 3.68 |
| alanine | 2.35 |
| valine | 2.49 |
| isoleucine | 2.25 |
| leucine | 4.4 |
| tyrosine | 2.62 |
| phenylalanine | 2.93 |
| lysine | 2.68 |
| histidine | 2.05 |
| arginine | 10.21 |
| tryptophan | 1.02 |

Molecular mass of the protein: 13,133 Da (MALDI-TOF-MS analysis).
Heavy metals: As+Cd+Cr+Ni+Hg+Pb+Se+Sn<15 ppm.

EXAMPLE 2

Preparation of a Derivatized, Cationised Guar Protein Extract

Modification of a guar protein extract in order to introduce cationic trimethylammonium groups. The guar protein extract of Example 1 is used as a starting compound.

160 ml of demineralised water, and then 0.75 g of sodium hydroxide tablets, are introduced into a 1 liter double-wall glass reactor, equipped with a mechanical stirrer and upward condenser. The stirrer is started at 50 revolutions per minute in order to dissolve the solid sodium hydroxide. Once the sodium hydroxide dissolves, 30 g of guar protein extract powder, with a moisture content of 7.3% by mass, are added.

The reactor is then brought to 60° C. throughout by circulating a hot heat-transfer fluid inside the double wall. After 1 hour of stirring at 60° C., a volume of ml of Quab® 151 (70% solution by mass of 2,3-epoxypropyl trimethylammonium chloride in water, sold by the company Degussa) is added dropwise over 20 minutes. After this addition, the reaction mixture is stirred at a temperature of 60° C. for 5 hours.

After cooling back to the room temperature, glacial acetic acid is added to the reaction medium until a pH equal to 7 is achieved.

The contents of the reactor are transferred into a separator funnel and added in drops to 2 liters of agricultural absolute ethanol while stirring. A precipitate forms. This solid is washed by a succession of 3 sequences of the operations of decanting, removal of the supernatant, and replacement into a suspension in 1.5 liters of fresh ethanol. Finally, the solid is dried in a filter funnel made of fritted glass of porosity 2. Said solid is dried for 16 hours at 45° C. under a 200 mbar vacuum, altered to 180 mbar with nitrogen. 21.6 g of powdered solid are finally obtained.
Properties of the Cationised Guar Protein
Isoelectric Point of the Cationised Protein Extract (in the Absence of Salt)

The isoelectric point of the cationised protein extract of Example 1 was determined by measuring the transmittance of the solution, by means of a UV-V is spectrophotometer set at 600 nm, as a function of the pH measured by a pH meter.

A graph is created to show the effect of the pH on the turbidity and thus the solubility of a 0.5% solution of cationised guar protein in demineralised water.

No precipitation is observed, but at a pH of 11.4 the solution becomes very turbid and the transmittance is then zero. Then, by increasing the pH, the solution is caused to become clearer. The isoelectric point of the cationised protein is shifted to higher pH values (to a pH of approximately 11.4) because of the cationisation.

The isoelectric point of the cationised protein extract is therefore in the region of pH 11.4.

EXAMPLE 3

Shampoos and Formulability

The conventional formulation used comprises the following ingredients:
0.3% cationised guar protein extract;
2% amphoteric surfactant;
14% anionic surfactant;
1-2% NaCl salt;
water to make the formulation up to 100%.

The surfactants used:
CAPB: cocamidopropyl betaine (amphoteric surfactant);
SLES: Sodium laurylethersulphate (anionic surfactant).

Procedure

The procedure to obtain an appropriate shampoo formulation is as follows:
- mix the protein into water in a beaker, and stir until dissolving occurs (length of time very variable according to the polymer, may require modification of the pH);
- add salt, and stir until dissolving occurs;
- meanwhile, mix the two surfactants in another beaker for 30 minutes;
- pour the water containing the salt and the polymer into the beaker containing the surfactants. Stir for 2 hours;
- adjust the pH to be between 5.5 and 6.5 with sodium hydroxide or citric acid.

The invention claimed is:

1. A substituted guar protein extract of guar meal having substituent groups grafted onto the amino acid functional groups of said protein extract, said guar protein extract comprising at least 65% by weight of proteins, and said guar protein extract being obtained by a process of concentration and/or extraction and/or isolation starting from guar meal.

2. The guar protein extract as defined by claim 1, said substituent grafted groups comprising cationic or cationizable groups.

3. The guar protein extract as defined by claim 2, said cationic, or cationizable groups comprising quaternary ammoniums or tertiary amines, pyridiniums, guanidiniums, phosphoniums or sulphoniums.

4. The guar protein extract as defined by claim 2, said cationic or cationizable groups being grafted onto the guar protein extract via a nucleophilic substitution reaction.

5. The guar protein extract as defined by claim 2, said cationic or cationizable groups being grafted onto the guar protein extract via esterification with an amino acid, or with a derivative of a quaternized amino acid.

6. The guar protein extract as defined by claim 5, said esterification being with glycine, lysine, arginine, 6-aminocaproic acid or betaine hydrochloride.

7. The guar protein extract as defined by claim 2, said cationic or cationizable groups being grafted onto the guar protein extract via a radical polymerization which comprises the grafting of monomers containing at least one cationic or cationizable group.

8. The guar protein extract as defined by claim 7, said monomers containing at least one cationic or cationizable group employed to conduct such radical polymerization being selected from among the following compounds of formulae (I), (II), (III) or (IV):

the compound of general formula (I)

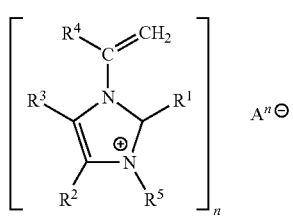

wherein:
$A^{n\ominus}$ is a $Cl^\ominus$, $Br^\ominus$, $I^\ominus$, $SO_4^{2\ominus}$, $CO_3^{2\ominus}$, $CH_3$—$OSO_3^\ominus$, $OH^\ominus$ or $CH_3$—$CH_2$—$OSO_3^\ominus$ ion, $R^1$ to $R^5$, which may be the same or different, are each an alkyl radical having to 20 carbon atoms, a benzyl radical or an H atom, and
n=1 or 2, or
the compound of general formula (II)

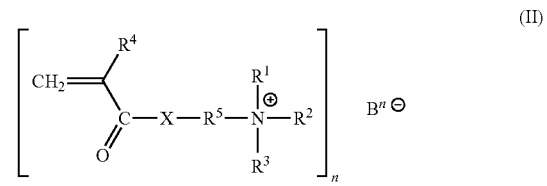

wherein:
X is a —NH group or an oxygen atom O,
$R^4$ is a hydrogen atom or an alkyl radical having 1 to 20 carbon atoms,
$R^5$ is an alkene radical having 1 to 20 carbon atoms,
$R^1$, $R^2$, $R^3$, which may be the same or different, are each an alkyl radical having 1 to 20 carbon atoms,
$B^{n\ominus}$ is a $Cl^\ominus$, $Br^\ominus$, $I^\ominus$, $SO_4^{2\ominus}$, $CO_3^{2\ominus}$, $CH_3$—$OSO_3^\ominus$, $OH^\ominus$ or $CH_3$—$CH_2$—$OSO^\ominus$ ion, and
n=1 or 2, or
the compound of general formula (III)

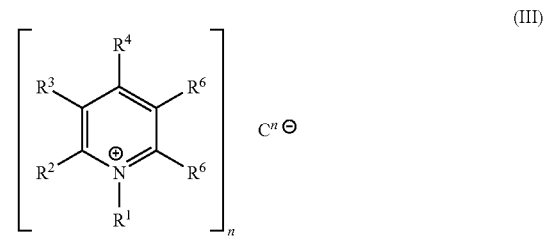

wherein:
$R^1$ to $R^6$, which may be the same or different, are each a hydrogen atom or an alkyl radical having 1 to 20 carbon atoms, with the proviso that one of $R^1$ to $R^6$ is a —CH=$CH_2$ radical,
$C^{n\ominus}$ is a $Cl^\ominus$, $Br^\ominus$, $I^\ominus$, $SO_4^{2\ominus}$, $ClH_3$—$OSO_3^\ominus$, $OH^\ominus$ or $CH_3$—$CH_2$—$OSO_3^\ominus$ ion, and
n=1 or 2, or
the compound of general formula (IV)

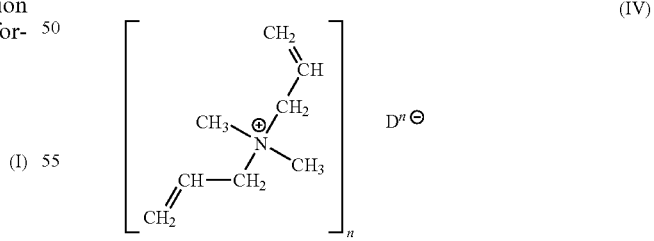

wherein:
$D^{n\ominus}$ is a $Cl^\ominus$, $Br^\ominus$, $I^\ominus$, $SO_4^{2\ominus}$, $CH_3$—$OSO_3^\ominus$, $OH^\ominus$ or $CH_3$—$CH_2$—$OSO_3^\ominus$ ion, and
n=1 or 2.

9. The guar protein extract as defined by claim 7, said monomers containing at least one cationic or cationizable group employed to conduct such radical polymerization being selected from among:

2-dimethylaminoethyl acrylate (DMAA),
quaternized 2-dimethylaminoethyl acrylate (Quat-DMAA),
2-dimethylaminoethyl methacrylate (DMAMA),
quaternized 2-dimethylaminoethyl methacrylate (Quat-DMAMA),
quaternized 2-diethylaminoethyl methacrylate chloride,
diallyldimethylammonium chloride (DADMAC),
methacrylamidopropyl trimethylammonium chloride, or mixtures thereof.

10. The guar protein extract as defined by claim 1, said substituent grafted groups comprising anionic or anionizable groups, uncharged hydrophilic or hydrophobic groups, or groups crosslinking the guar protein extract, optionally polymeric groups.

11. The guar protein extract as defined by claim 1, comprising from 65% to 95% by weight of proteins.

12. The guar protein extract as defined by claim 11, comprising from 65% to 85% by weight of proteins.

13. The guar protein extract as defined by claim 1, said protein extract comprising:
    10% to 30% glutamic acid;
    5% to 25% arginine;
    5% to 20% aspartic acid;
    1% to 10% leucine;
    1% to 8% glycine;
these percentages being expressed by mass based on the total mass of amino acids contained in the extract.

14. A formulation comprising the substituted guar protein extract as defined by claim 1.

15. The formulation as defined by claim 14, comprising a:
    cosmetic composition,
    pharmacological composition,
    composition for a household treatment,
    coating composition
    paint,
    food composition,
    lubricant composition,
    fluid useful for oil and gas extraction,
    phytosanitary composition, or
    water treatment composition.

16. The formulation as defined by claim 14, comprising:
    an agent for the treatment and/or modification of surfaces,
    a dispersing agent,
    an emulsifier,
    an agent to prevent rebound, washing away, or blowing away of phytosanitary formulations,
    an adhesive,
    a flocculant,
    a surfactant,
    an agent for altering the properties of foams,
    a foam stabilizer,
    an agent for modifying the appearance of a coating, and/or
    a thickener.

17. The guar protein extract as defined by claim 2, said cationic or cationizable groups being combined with negatively charged counter ions selected from among chloride, bromide, iodide, fluoride, sulphate, methylsulphate, phosphate, hydrogenophosphate, phosphonate, carbonate, hydrogenocarbonate, or hydroxide ions.

18. A process for the preparation of a substituent guar protein extract as defined by claim 1, comprising the following steps:
    a) providing a guar protein extract of guar meal;
    b) grafting substituents onto the amino acid functional groups contained in the protein extract; and optionally c) recovering the substituted protein extract.

* * * * *